US009625425B2

(12) United States Patent
Stewart et al.

(10) Patent No.: US 9,625,425 B2
(45) Date of Patent: Apr. 18, 2017

(54) BOND INSPECTION SYSTEM AND METHOD

(71) Applicant: The Boeing Company, Chicago, IL (US)

(72) Inventors: Alan Frank Stewart, Seattle, WA (US); Marc Joel Piehl, Renton, WA (US); Douglas Allen Frisch, Renton, WA (US); Kevin R. Housen, Tacoma, WA (US); William J. Sweet, Seattle, WA (US)

(73) Assignee: The Boeing Company, Chicago, IL (US)

( * ) Notice: Subject to any disclaimer, the term of this patent is extended or adjusted under 35 U.S.C. 154(b) by 212 days.

(21) Appl. No.: 14/699,474

(22) Filed: Apr. 29, 2015

(65) Prior Publication Data

US 2016/0320350 A1    Nov. 3, 2016

(51) Int. Cl.
*G01N 29/24* (2006.01)
*G01K 11/02* (2006.01)
(Continued)

(52) U.S. Cl.
CPC .............. *G01N 29/28* (2013.01); *G01N 3/00* (2013.01); *G01N 29/2418* (2013.01);
(Continued)

(58) Field of Classification Search
CPC ...... G01N 29/28; G01N 29/2418; G01N 3/00; G01N 2291/267; G01N 2291/02827; G10K 11/02
(Continued)

(56) References Cited

U.S. PATENT DOCUMENTS 4,944,185 A * 7/1990 Clark, Jr. ............... G01N 29/12
324/214
5,245,293 A * 9/1993 Runner ............... G01N 27/225
156/64
(Continued)

FOREIGN PATENT DOCUMENTS

WO    2014/102773    7/2014

OTHER PUBLICATIONS

Mann, A. B. et al.; "Modeling and characterizing the propagation velocity of exothermic reactions in multilayer foils"; J. Appl. Phys. 82(3), Aug. 1, 1997; pp. 1178-1188; American Institute of Physics.
(Continued)

*Primary Examiner* — J M Saint Surin
(74) *Attorney, Agent, or Firm* — Thompson Hine LLP

(57) ABSTRACT

A bond inspection system may include a material that reacts to applied activation energy by creating a compression wave, the material positioned adjacent a surface of a structure having a bond to be inspected and shaped in a predetermined pattern, such that reaction of the material causes compression waves to travel through the surface and structure; a source of activation energy capable of directing the activation energy at the material; and a controller programmed to actuate the source of activation energy to direct the activation energy at discrete portions of the predetermined pattern of material in a predetermined sequence selected to create a plurality of the compression waves so that the compression waves reflect from an opposite side of the structure as a plurality of tension waves that combine at substantially the same time at a bondline of the structure to be inspected.

20 Claims, 2 Drawing Sheets

(51) Int. Cl.
    *G01N 3/00*         (2006.01)
    *G01N 29/28*       (2006.01)
    *G10K 11/02*       (2006.01)

(52) U.S. Cl.
    CPC .... *G10K 11/02* (2013.01); *G01N 2291/02827* (2013.01); *G01N 2291/267* (2013.01)

(58) Field of Classification Search
    USPC .......................................................... 73/588
    See application file for complete search history.

(56) References Cited

U.S. PATENT DOCUMENTS

| | | | |
|---|---|---|---|
| 5,902,935 A * | 5/1999 | Georgeson | G01N 29/2412 73/801 |
| 6,848,321 B2 * | 2/2005 | Bossi | G01N 3/00 73/788 |
| 7,507,312 B2 | 3/2009 | Bossi et al. | |
| 2008/0037808 A1 * | 2/2008 | Sawada | B06B 1/0622 381/190 |
| 2011/0283767 A1 * | 11/2011 | Questo | G01N 29/12 73/1.82 |
| 2014/0049773 A1 | 2/2014 | Lahrman et al. | |

OTHER PUBLICATIONS

Picard, Yoosuf N. et al.; "Pulsed laser of reactive multilayer films"; Applied Physics Letters 88, 144102 (2006); pp. 144102-1-144102-3; American Institute of Physics.

* cited by examiner

BOND INSPECTION SYSTEM AND METHOD

TECHNICAL FIELD

This disclosure relates to systems and methods for testing the strength of materials and, more particularly, to systems and methods for non-destructive testing of bonds formed within composite materials.

BACKGROUND

Carbon fiber reinforced polymer (CFRP) composites are fiber reinforced composite materials that use carbon fiber as a primary structural component. CFRP composites use thermosetting resins, such as epoxy, polyester, or vinyl ester. The polymer is impregnated or coated on a woven carbon fiber cloth to provide a lightweight and strong material compared to other materials such as steel and aluminum. Consequently, CFRP composites are used where strong, lightweight structural materials are advantageous, such as in the aircraft and aerospace industries.

When fabricating CFRP structures, it is necessary to bond CFRP components with adhesives. Since such structures may be used to support loads in aircraft and other vehicles, it is necessary to test the strength and integrity of the bonds of CFRP composite structures. It is also preferable to test the integrity of such bonds non-destructively, in view of the cost of CFRP structures, and if possible to test the integrity of the bonds at the jobsite.

Systems have been developed to nondestructively test the integrity of bonds formed within a composite structure. For example, a laser bond inspection device, or LBID, utilizes a laser that is directed at a polyvinylchloride (PVC) tape that has been adhesively attached to the surface of the composite structure at the site of the bond to be inspected. The energy from the laser ablates the tape, creating compression waves that travel through the composite structure to be reflected from an opposite surface of the structure as tension waves. The tension waves stress the bondline and the resultant surface motion of the composite structure is detected by a velocity interferometer system for any reflector (VISAR), which measures velocity on the surface of the bonded structure.

A disadvantage with such LBID systems is that they require a relatively large laser—on the order of 40-50 joules—to project laser energy to ablate the PVC tape to generate compression waves capable of testing the integrity of the bondline of the composite structure. Such large lasers may be difficult to move to a job site to inspect a structure, are relatively costly, and require relatively large amounts of power to operate.

Accordingly, there is a need for a non-destructive bond inspection system and method that is relatively compact, low cost, and requires less power than conventional LBID systems.

SUMMARY

In one embodiment, a bond inspection system may include a material that reacts to applied activation energy by creating a compression wave, the material positioned adjacent a surface of a structure having a bond to be inspected and shaped in a predetermined pattern, such that reaction of the material causes compression waves to travel through the surface and structure, a source of activation energy that directs the activation energy at the material, and a controller programmed to actuate the source of activation energy to direct the activation energy at discrete portions of the predetermined pattern of material in a predetermined sequence selected to create a plurality of the compression waves so that the compression waves reflect from an opposite side of the structure as a plurality of tension waves that combine at substantially the same time at a bondline of the structure to be inspected.

In another embodiment, a bond inspection system may include a transducer having a transducer plate and an acoustic impedance matching layer shaped to engage an outer surface of a structure having a bond to be inspected, a material that reacts to laser energy, the material applied to an upper surface of the transducer plate, such that reaction of the material causes compression waves to travel through the transducer to a structure to be inspected, a source of laser energy, the source positioned to direct laser energy at the material, and a controller programmed to actuate the source of laser energy to direct laser energy to impact the material to create the plurality of compression waves of intensity sufficient to reflect from an opposite side of the structure to be inspected as a plurality of tension waves at a bondline of the structure to be inspected.

In yet another embodiment, a method for inspecting a bondline of a structure may include selecting a material that reacts to applied activation energy by creating a compression wave, positioning the material in a predetermined pattern adjacent a surface of the structure, such that reaction of the material causes compression waves that travel through the surface and structure to the bondline, and actuating a source of activation energy by a controller programmed to direct activation energy to impact discrete portions of the predetermined pattern of the material in a predetermined sequence selected to cause the material to react to create the plurality of compression waves so that the compression waves reflect from an opposite side of the structure as a plurality of tension waves that combine at substantially the same time at the bondline.

Other objects and advantages of the disclosed bond inspection system and method will be apparent from the following description, the accompanying drawings, and the appended claims.

DETAILED DESCRIPTION

Figure 1:
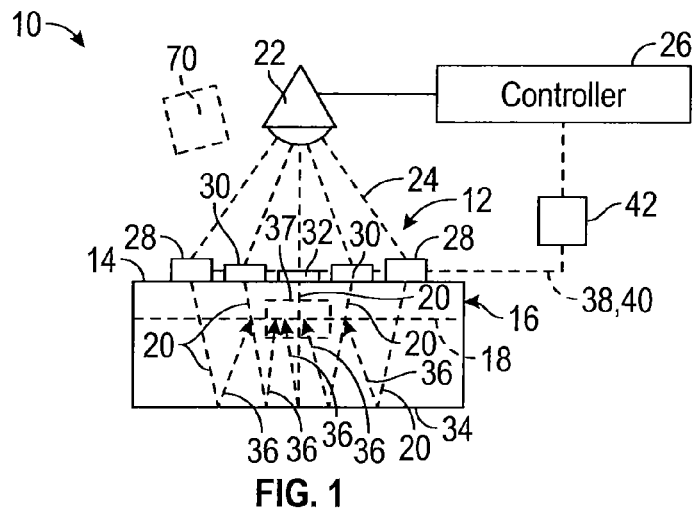
FIG. 1 is a schematic side elevation of an embodiment of the disclosed bond inspection system, in which a reactive material is attached directly on a surface of a structure having a bond to be inspected.

As shown in FIG. 1, the disclosed bond inspection system, generally designated 10, may include a material, generally designated 12, that reacts to applied activation energy by creating a compression wave. The material 12 may be positioned adjacent a surface 14 of a structure 16 having a bond 18 to be inspected. In an embodiment, the material 12 may be shaped in a predetermined pattern, such that reaction of the material causes compression waves 20 to travel through the surface 14 and the structure 16.

The system 10 also may include a source of activation energy, which in embodiments may take the form of a laser 22 that is capable of directing the activation energy, represented by laser beams 24, at the material 12. The system 10 also may include a controller 26 that may be programmed to actuate the source 22 of activation energy to direct the activation energy 24 at discrete portions 28, 30, 32 of the predetermined pattern of material 12 in a predetermined time sequence selected to create a plurality of compression waves 20 so that the compression waves reflect from a second surface, which in embodiments may take the form of an opposite side 34 of the structure 16, as a plurality of tension waves 36 that combine at substantially the same time at the bondline 18 of the structure.

In another embodiment, the source of activation energy may take the form of an exploding wire 38, or a conductive wire 40 that receives energy from a detonator 42 that is controlled by the controller 26. The exploding wire 38 or conductive wire 40 may be connected to the reactive material 12 so that the material may be caused to react by the controller 26 in the predetermined sequence. In an embodiment, the controller 26 may cause the discrete portions 28, 30, 32 to react in a predetermined time sequence.

Figure 6:
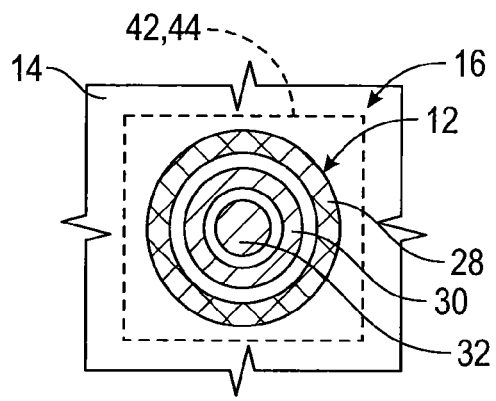
FIG. 6 is a schematic detail showing a top plan view of the embodiments of FIGS. 1 and 3.

As shown in FIGS. 1 and 6, the predetermined pattern of reactive material 12 may include a shape in which the discrete portions 28, 30, 32 take the form of a plurality of concentric rings that may be centered over a predetermined location of the bondline 18 that is to be inspected. Alternately, innermost ring 32 may take the form of a dot or circle, as shown in FIGS. 1 and 6. In an embodiment, the thickness of each of the rings 28, 30, 32 may vary. In a more specific embodiment, the outermost ring 28 may be the thickest, and the thickness of each of the rings may decrease in a radially inward direction toward a center of the predetermined pattern, so that the center ring 32 is the thinnest. Accordingly, the amount of reactive material 12 in each of the rings 28, 30, 32 may be reduced, on a per unit of area of the rings, for each of the rings in comparison to a next outermost ring.

Compression waves 20 from an outer ring, such as outermost ring 28, must traverse a greater distance through the structure 16 to reach the area 37 of the bondline 18 of interest as a tension wave 36 than ring 30, and thus dissipate in energy more than radially inner rings 30, 32. Similarly, the compression waves 20 from ring 30 must traverse a greater distance through the structure 16 to reach the area 37 of interest as tension wave 36 than ring 32, and thus dissipate in energy more than a tension wave 36 from innermost ring 32. By selecting the thickness, and hence amount of reactive material 12 per unit area of the rings 28, 30, 32 to decrease in a radially inward direction, the intensity of the tension waves 36 reaching the area of interest 37 created by the rings may be made to be approximately equal.

In an embodiment, the controller 26 may be programmed to cause the source of activation energy, which in FIG. 1 may be a laser 22, to actuate the plurality of concentric rings 28, 30, 32 a sequence such that the tension waves 36 reach the portion of the bondline to be inspected approximately simultaneously. In a specific embodiment, the controller 26 may be programmed to actuate the reactive material 12 wherein the sequence actuates the concentric rings 28, 30, 32 so that a radially outermost one of the concentric rings is actuated by the source of activation energy first, then successively radially inner ones of the concentric rings are actuated sequentially toward a radially innermost one of the concentric rings. Although FIGS. 1 and 6 show three rings 28, 30, 32, it is within the scope of the disclosure to provide a greater number of rings or a fewer number of rings. Further, it is within the scope of the disclosure to provide different patterns than concentric rings, such as a series of concentric groupings of discrete dots of reactive material 12, or segmented rings of reactive material.

In the embodiment of FIG. 1, and as shown in FIG. 6, the reactive material 12 may be applied directly to the surface 14 of the structure 16 having the bond 18 to be inspected. As shown in FIG. 6, the reactive material 12 may be encased in a polyvinylchloride (PVC) tape 42, or encased in a metal foil 44, each of which may in turn be attached directly to the surface 14 of the structure 16 by a suitable adhesive for temporarily bonding the tape to the surface. In embodiments, the reactive material 12 may be selected from lead azide and silver azide. By choosing such a reactive material 12, the size of the source of activation energy may be reduced because the reactive material contributes energy to the creation of the compression waves 20. For example, if the source of activation energy is a laser 22, that laser need only be a 10 joule laser, or a laser that generates less than 10 joules to develop compression waves 20 of sufficient force to create the necessary tension waves 36.

The reactive material 12 is selected to provide a chemical reaction when activated by the source of activation energy, which in embodiments may be a laser 22. The products of the chemical reaction of the reactive material 12, which may be products of combustion or rapid oxidation that may include carbon dioxide ($CO_2$) and water vapor, add chemical energy to the creation of compression waves 20 in the structure 16, thereby reducing the power and energy required of the source of activation energy to create compression waves 20 of comparable amplitude to prior art methods that do not employ reactive material 12. For example, certain prior art methods may utilize a laser that ablates a PVC tape. Such ablation is not a chemical reaction and does not generate chemical energy that contributes to the energy of the compression waves formed by, for example, a laser to the extent the chemical energy from the chemical reaction (which may be rapid oxidation) of the reactive material 12 of the disclosed method and system 10.

Figure 2:
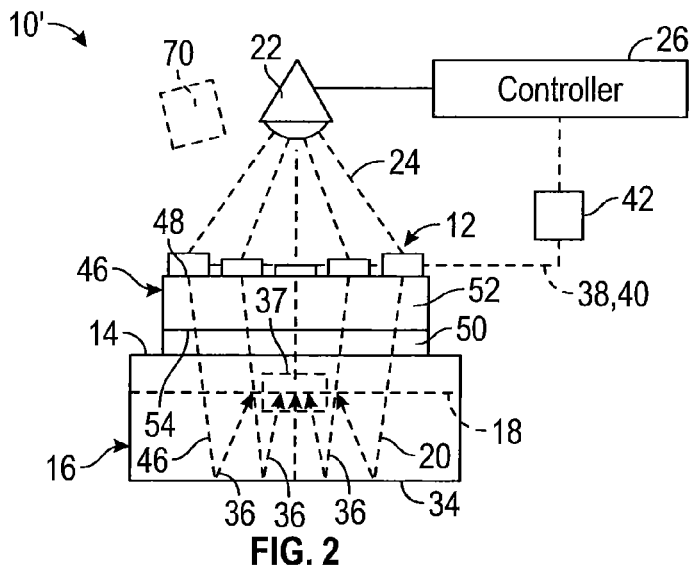
FIG. 2 is a schematic side elevation of another embodiment of the disclosed bond inspection system, in which the reactive material is mounted on a transducer that is attached directly to the structure having a bond to be inspected.

As shown in FIG. 2, in another embodiment, the system 10' may include a transducer, generally designated 46. The transducer 46 may be mounted on or attached directly to the structure 16 having a bondline 18 to be inspected. In a particular embodiment, the reactive material 12 may be applied to an outer surface 48 of the transducer 46. In an embodiment, the transducer 46 may include an acoustic impedance matching layer 50 and a transducer plate 52. The acoustic impedance matching layer 50 may be mounted on or attached directly to the surface 14 of the structure 16, and to the underside 54 of the transducer plate 52, by suitable adhesives.

In an embodiment, the acoustic impedance matching layer 50 may have a thickness that is approximately one-quarter the length of a wavelength of a compression wave 20 propagating through the acoustic impedance matching layer 50 and created by actuation by the source of activation energy, such as laser 22, of the reactive material 12 that is attached to or bonded to transducer 46.

In an embodiment, the acoustic impedance matching layer 52 may be selected to have an impedance which is equal to, or closely approximates, the geometric mean of the impedances of the two media that it connects. In in the embodiment of FIG. 2, a preferred impedance of the acoustic impedance matching layer 52 may be the geometric mean of the impedance of the transducer plate 52 and the impedance of the structure 16 having a bond to be inspected. The geometric mean may be determined by the following formula:

$$Z_{aiml} = \sqrt{Z_{cfrp} \times Z_{Al}}$$

where: $Z_{aiml}$=the impedance of the acoustic impedance matching layer, $Z_{cfrp}$=the impedance of the carbon fiber reinforced polymer structure 16, and $Z_{Al}$=the impedance of the transducer plate 52 if made of aluminum.

In this particular example, the impedance of the carbon fiber reinforced polymer structure 16 is $4.7 \times 10^5$ g/(cm$^2$-s), and the impedance of the aluminum transducer plate 52 is $1.7 \times 10^6$ g/(cm2-s). Accordingly, using the above formula, an optimal impedance for the acoustic impedance matching layer 52 ($Z_{aiml}$)≈$8.1 \times 10^5$ g/(cm2-s). An appropriate material for the acoustic impedance matching layer 50 would be magnesium, which closely matches the optimum acoustic impedance with an impedance ($Z_{mg}$) of $10^6$ g/(cm$^2$-s).

The velocity of a compression wave traveling through magnesium ($V_{mg}$) is approximately $5.8 \times 10^5$ cm/sec, and therefore an appropriate impedance matching layer for aluminum and CFRP would be approximately 0.6 mm thick magnesium foil. Further, use of magnesium foil for the acoustic impedance matching layer 50 would be matched with a laser 22 embodiment of the source of activation energy that transmits a 200 nsec laser pulse width to generate a wave form with a frequency of 2.5 Mhz, because the frequency of the compression wave 20 generated by such a laser pulse 24 is approximately twice the pulse width of the laser pulse.

Figure 3:
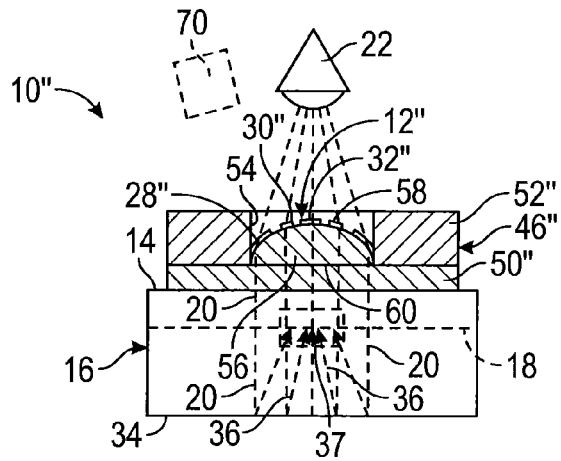
FIG. 3 is a schematic side elevation in section of yet another embodiment of the disclosed bond inspection system, in which the transducer includes a lens.

As shown in FIG. 3, in a third embodiment of the inspection system, generally designated 10", the transducer 46" may include a recess 54, which may be located centrally on the transducer plate 52", that receives a lens 56. The lens 56 may be oriented to have a convex upper surface 58 and a substantially flat bottom surface 60 that is attached to the acoustic impedance matching layer 50". With this embodiment, the recess 54 may pass completely through the transducer plate 52", and the lens 56 may be attached to the acoustic impedance matching layer 50" and/or to the surface of the transducer plate defining the recess.

Alternatively, the transducer plate 52" of the transducer 46" may be machined to have a centrally located recess 54 in which the lens 56 is machined in the center of the recess. Accordingly, in this embodiment the lens 56 is unitary with the transducer plate 52", and would not have to be separately attached to the acoustic impedance matching layer 50" to hold it in place. With either embodiment, the lens 56 is positioned within the recess 54 formed in the transducer plate 52", a bottom surface thereof contacts the acoustic impedance matching layer 50", and the lens preferably is made of the same material as the remainder of transducer plate.

As with the embodiment of FIG. 2, the acoustic impedance matching layer 50" of the transducer 46" of FIG. 3 may be attached directly to the upper surface 14 of the structure 16. The lens 56 and transducer plate 52" may be attached to the acoustic impedance matching layer 50", and the acoustic impedance matching layer may be attached to the upper surface 14 of the structure 16 by suitable adhesives. In an embodiment, the lens 56 may be made of the same material as the remainder of the transducer plate 52", which in an embodiment may be aluminum, or alternatively, may be made of a different material than the remainder of the transducer plate.

Figure 4:
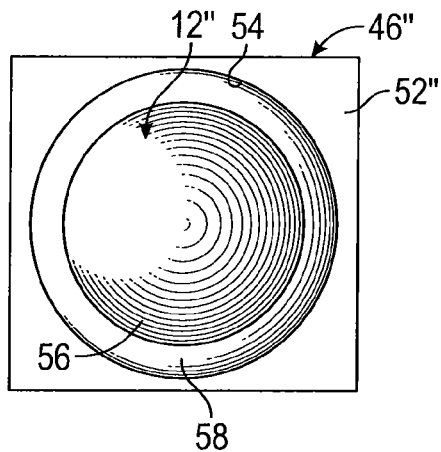
FIG. 4 is a schematic top plan view of the transducer of the embodiment of FIG. 3.

The reactive material 12" may be applied directly to the upper surface 58 of the lens 56. In one aspect, the reactive material 12" may take the form of concentric rings 28", 30", 32", as shown in FIG. 3. In another aspect, shown in FIG. 4, the reactive material 12" may take the form of a continuous coating that may have a circular or disk shape applied continuously over the upper surface 58 of the lens 56. In an embodiment, the shape and curvature of the convex upper surface 58 of the lens 56 is selected such that a distance from any point on the upper surface to the area of interest 37 of the bondline 18, after reflection from the opposite side 34 of the structure 16, is equal or is substantially equal.

Accordingly, when the reactive material 12, 12" is activated by the source of activation energy, which may be a laser 22, the reactive material 12, 12" may be activated simultaneously or substantially simultaneously by laser activation energy 24. The lens 56 is shaped such that a distance from each point of the convex upper surface 58, after reflection from the opposite side 34 of the structure 16, to an area of interest 37 of a bondline 18 of the structure, is substantially equal. Accordingly, with the embodiment of FIGS. 3 and 4, there may be no need for precise sequencing of activation of the laser 22 by the controller 26, or in alternate embodiments, activation of the exploding wire 38, or conductive wire 40 (see FIGS. 1 and 2).

Figure 5:
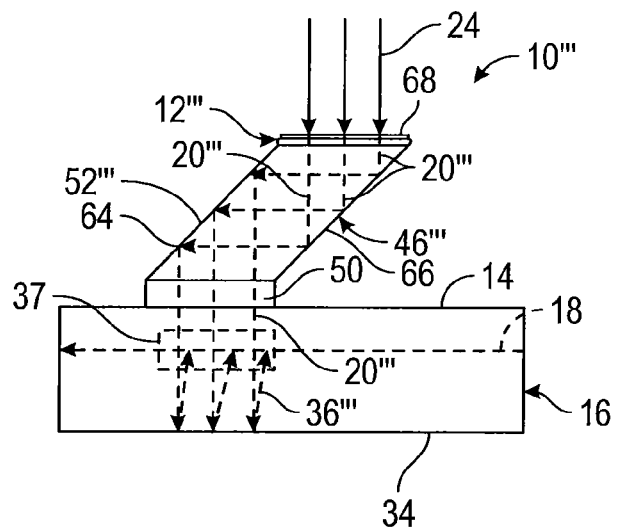
FIG. 5 is a schematic side elevation of still another embodiment of the disclosed bond inspection system, in which the transducer is in the form of a parallelepiped having oblique angles.

As shown in FIG. 5, in yet another embodiment of the bond inspection system, generally designated 10''', the transducer 46''' may include a transducer plate 52''' having the shape of a parallelepiped having two opposing, oblique-angled sides 64, 66. The transducer plate 52''' may be mounted on the acoustic impedance matching layer 50 by an adhesive, and the acoustic impedance matching layer may in turn be adhesively attached to the upper surface 14 of the structure 16. The source of activation energy, such as laser 22 (see FIGS. 1, 2, and 3) may be oriented and activated by controller 26 to transmit a laser activation energy 24 that impinges on the reactive material 12''' generating compression waves 20'''. In other aspects, the source of activation energy may take the form of an exploding wire 38, or conductive wire 40, may be connected to the reactive material 12''' as in FIGS. 1 and 2.

The compression waves 20''' may travel through the transducer plate 52''' and are reflected first off of side wall 66, and then are directed to be reflected off of opposite side wall 64. The compression waves 20''' reflected off of side was 64 are reflected downwardly through the acoustic impedance matching layer 50 and through the structure 16 to be reflected off of the bottom surface 34 of the structure and back upwardly as tension waves 36 to the bondline 18 to be inspected. An advantage of this embodiment is that the shape of the transducer plate 46''' enables the system 10''' to be utilized in a space that may have a restricted access to the surface 14 in order to inspect a particular region 62 of the bondline 18 where line-of-sight access may be difficult, such as where the area of interest 37 of the bondline 18 of the structure 16 is offset from an access port. The transducer 46''' of FIG. 5 allows for lateral offset from the area of interest 37, as well as vertical offset where the laser 22 and reactive material 12''' interact.

In a further embodiment, a damping layer 68 may be applied to cover all or substantially all of the upper surface of the reactive material 12'''. The damping layer 68 may take the form of a water layer in an embodiment, and in alternate embodiments may take the form of a clear tape, or a piece of glass plate. The benefit of such a damping layer 68 is that the damping layer, such as a water layer, may act to compress the expanding plasma created when the reactive material 12''' is activated by the laser energy 24. This confinement of the plasma may reflect the shockwave back into the transducer 46'''.

A method for inspecting a bondline 18 of a structure 16 utilizing the system 10, 10', 10'', 10''' may include initially selecting a reactive material 12, 12'', 12''', and positioning that reactive material in a predetermined pattern adjacent the surface 14 of the structure 16, such that reaction of the reactive material 12, 12'', 12''' causes compression waves that travel through the surface and structure to the bondline 18 to be inspected.

In an embodiment as shown in FIG. 1, the positioning may take the form of attaching or applying the reactive material 12 directly to the surface 14 by an adhesive, or in the form of a PVC tape or metal foil. In other embodiments, the positioning may take the form of mounting or attaching the reactive material 12, 12'', 12''', to a transducer 46, 46'', 46'''. In some embodiments, such as that shown in FIGS. 2 and 3, the positioning may take the form of applying the material 12, 12'' to the transducer 46, 46'', in a predetermined pattern, such as a series of concentric rings 28, 30, 32, to the upper surface 48 of the transducer 46, 46''.

In a particular embodiment, the reactive material 12'' may be applied to the upper surface 58 of a lens 56 received in the transducer plate 52'' (FIG. 3). In each embodiment, the reactive material 12, 12'', 12''' may be applied directly above or adjacent an area of interest 37 of the bondline 18 to be inspected.

A source of activation energy, which may take the form of a laser 22, exploding wire 38, or powered wire 40, may be actuated by a controller 26 programmed to direct activation energy, which in an embodiment may be laser energy 24, to impact discrete portions 28, 28''  30, 30'', 32, 32'' of the predetermined pattern of reactive material 12, 12'', 12''' in a predetermined timed sequence. The sequence may be selected to cause the material to react to create a plurality of compression waves 20 that travel through the structure 16 to reflect from an opposite side 34, or underside, of the structure 16 as tension waves 36 that impact the area of interest 37 of the bondline 18.

In embodiments, the resultant tension waves 36 may be detected by a VISAR device, generally designated 70 in FIGS. 1, 2, and 3. The controller 26 may be programmed to activate the discrete portions 28, 30, 32 of the reactive material 12, or discrete portions of the reactive material 12''' (FIG. 5), such that the tension waves 36, 36''' reflected from the opposite side 34 of the structure 16 combine at the area of interest 37 at substantially the same time. This simultaneity of arrival of the tension waves 36, 36''' at the area of interest 37 may be accomplished by the controller 26 causing the laser 22 to sequentially activate the discrete portions 28, 30, 32, or by placing the reactive material 12'' on the convex outer surface 58 of a lens 56 that forms part of a transducer 46''.

While the forms of apparatus and methods described herein constitute preferred embodiments of the disclosed system and method for bond inspection, it is to be understood that the disclosure is not limited to these precise forms of apparatus and methods, and the changes may be made therein without departing from the scope of the disclosure.

What is claimed is:

1. A bond inspection system, the system comprising:
a material that reacts to applied activation energy by creating a compression wave, the material positioned adjacent a surface of a structure having a bond to be inspected and shaped in a predetermined pattern, such that reaction of the material causes compression waves to travel through the surface and the structure;
a source of activation energy that directs the activation energy at the material; and
a controller programmed to actuate the source of activation energy to direct the activation energy at discrete portions of the predetermined pattern of material in a predetermined sequence selected to create a plurality of the compression waves so that the compression waves reflect from an opposite side of the structure as a plurality of tension waves that combine at substantially the same time at a bondline of the structure to be inspected.

2. The bond inspection system of claim 1, wherein the source of activation energy is selected from a laser, an exploding wire, and a conductive wire.

3. The bond inspection system of claim 1, wherein the predetermined pattern includes a plurality of concentric rings, and wherein each of the plurality of concentric rings forms one of the discrete portions of the predetermined pattern.

4. The bond inspection system of claim 3, wherein a thickness of each of the rings of the plurality of concentric rings decreases in a radially inward direction toward a center of the predetermined pattern, such that an intensity of each one of the compression waves created by the rings of the plurality of concentric rings decreases toward the center of the predetermined pattern and is approximately equal at a selected portion of the bondline to be inspected.

5. The bond inspection system of claim 3, wherein the controller is programmed to cause the source of activation energy to actuate the plurality of concentric rings in a sequence selected such that the tension waves reach a portion of the bondline to be inspected approximately simultaneously.

6. The bond inspection system of claim 5, wherein the sequence actuates the concentric rings so that a radially outermost one of the concentric rings is actuated by the source of activation energy first, then successive radially inner ones of the concentric rings are actuated sequentially toward a radially innermost one of the concentric rings.

7. The bond inspection system of claim 1, wherein the material is applied to the surface of the structure having a bond to be inspected.

8. The bond inspection system of claim 1, wherein the material is selected from lead azide and silver azide; and the material is in an applique form that is selected from polyvinyl chloride tape and metal foil tape that is applied to the surface of the structure having a bond to be inspected.

9. The bond inspection system of claim 1, further comprising a transducer mounted on the structure having a bond to be inspected; and wherein the material is applied to an outer surface of the transducer.

10. The bond inspection system of claim 9, wherein the transducer includes an acoustic impedance matching layer; and a transducer plate; and wherein the acoustic impedance matching layer is attached to the surface of the structure having a bond to be inspected and the underside of the transducer plate.

11. The bond inspection system of claim 10, wherein the acoustic impedance matching layer has a thickness that is approximately one-quarter the length of a wavelength of a compression wave propagating through the acoustic impedance matching layer that is created by actuation by the source of activation energy of the reactive material that is attached to the transducer.

12. The bond inspection system of claim 10, wherein the acoustic impedance matching layer is made of a material having an impedance approximately equal to a geometric mean of an impedance of the transducer plate and an impedance of the structure having a bond to be inspected.

13. The bond inspection system of claim 10, wherein the transducer plate is made of aluminum, the structure having a bond to be inspected is made of carbon fiber reinforced plastic, and the acoustic impedance matching layer is made of magnesium.

14. The bond inspection system of claim 10, wherein the transducer includes a lens having an outer, convex surface; and wherein the material is applied to the outer, convex surface.

15. The bond inspection system of claim 14, wherein the lens is positioned within a recess in the transducer plate, and a bottom surface of the lens contacts the acoustic impedance matching layer.

16. The bond inspection system of claim 15, wherein the material is distributed on the outer, convex surface such that the controller is programmed to actuate the source of activation energy to actuate all of the material simultaneously; and wherein the lens is shaped such that a distance from each point of the convex outer surface, after reflection from the opposite side of the structure, to an area of interest of a bondline of the structure, is substantially equal.

17. The bond inspection system of claim 10, wherein the transducer plate is in the shape of a parallelepiped having two opposing, oblique-angled sides.

18. A bond inspection system, the system comprising:
a transducer having a transducer plate and an acoustic impedance matching layer shaped to engage an outer surface of a structure having a bond to be inspected;
a material that reacts to laser energy, the material applied to an upper surface of the transducer plate, such that reaction of the material creates compression waves to travel through the transducer to a structure to be inspected;
a source of laser energy, the source positioned to direct laser energy at the material; and
a controller programmed to actuate the source of laser energy to direct laser energy to impact the material to create a plurality of the compression waves of intensity sufficient to reflect from an opposite side of the structure to be inspected as a plurality of tension waves at a bondline of the structure to be inspected.

19. A method for inspecting a bondline of a structure, the method comprising:
selecting a material that reacts to applied activation energy by creating a compression wave;
positioning the material in a predetermined pattern adjacent a surface of the structure, such that reaction of the material causes compression waves that travel through the surface and structure to the bondline; and
actuating a source of activation energy by a programmed controller to direct activation energy to impact discrete portions of the predetermined pattern of the material in a predetermined sequence selected to cause the material to react to create the plurality of compression waves so that the compression waves reflect from an opposite side of the structure as a plurality of tension waves that combine at substantially the same time at the bondline.

20. The method of claim 19, further comprising positioning the material on an upper surface of a transducer; and contacting the transducer to the surface of the structure.

* * * * *